United States Patent [19]
Meserol

[11] Patent Number: 5,492,674
[45] Date of Patent: Feb. 20, 1996

[54] EVANESCENT WAVE IMMUNOASSAY SYSTEM

[75] Inventor: Peter Meserol, Montville, N.J.

[73] Assignee: Boehringer Mannheim Corporation, Indianapolis, Ind.

[21] Appl. No.: 406,065

[22] Filed: Mar. 17, 1995

[51] Int. Cl.$^6$ .......................... G01N 21/01; G01N 21/64
[52] U.S. Cl. ..................... 422/82.08; 422/82.11; 436/527; 436/165
[58] Field of Search ..................... 436/518, 527, 436/165; 422/82.05, 82.08, 55, 56, 58, 82.11, 102; 356/244; 385/12, 137

[56] References Cited

U.S. PATENT DOCUMENTS

| | | | |
|---|---|---|---|
| 3,998,591 | 12/1976 | Eckfeldt | 23/253 R |
| 4,558,014 | 12/1985 | Hirschfeld | 436/527 |
| 4,716,121 | 12/1987 | Block | 436/514 |
| 4,880,752 | 11/1989 | Keck et al. | 435/64 |
| 4,902,629 | 2/1990 | Meserol | 436/165 |
| 4,909,990 | 5/1990 | Block | 422/82.11 |
| 4,978,503 | 12/1990 | Shanks et al. | 422/58 |
| 5,006,716 | 4/1991 | Hall | 250/458.1 |
| 5,015,092 | 5/1991 | Sting | 356/300 |
| 5,093,268 | 3/1992 | Leventis et al. | 436/172 |
| 5,152,962 | 10/1992 | Lackie | 422/681 |
| 5,156,976 | 10/1992 | Slovacek et al. | 436/164 |
| 5,168,156 | 12/1992 | Fischer et al. | 250/227.21 |
| 5,173,434 | 12/1992 | Morris et al. | 436/172 |

OTHER PUBLICATIONS

Bluestein, B. I. et al. "Evanescent Wave Immunosensors For Clinical Diagnostics", *Biosensors with Fiberoptics*, Wise and Wingard, 1991, The Humana Press, Inc., pp. 181–223.

Lackie, Steve J. et al., "Instrumentation for Cylindrical Waveguide Evanescent Fluorosensors", *Biosensors with Fiberoptics*, Wise and Wingard, 1991, The Humana Press, Inc. pp. 225–251.

*Primary Examiner*—Jeffrey R. Snay
*Attorney, Agent, or Firm*—Perman & Green

[57] ABSTRACT

Apparatus for assaying a fluid sample with radiation capable of exciting fluorescence in fluorescent material comprises a totally internally reflecting, unitary elongated substrate transmissive to both the excitation radiation and to the fluorescence. The fluorescent material includes at least a moiety of an antibody-antigen complex that includes a tag that will provide the fluorescence when excited by an evanescent wave generated by the excitation radiation. The substrate includes an elongated fiber and an integral lens formed to guide the optical radiation into the fiber within the bounds of a critical angle to assure total internal reflectance. A hollow elongated enclosure is disposed concentrically about and spaced from the fiber so as to provide an interspace of capillary dimensions. A test implement supports the elongated substrate, has a reservoir for receiving a fluid sample to be assayed, and is selectively movable to an operative position whereat the fluid sample is caused to flow onto the fiber and, by capillary action, into the interspace between the fiber and the enclosure. The apparatus further includes a source of the excitation radiation, refractive element for focusing the radiation toward the lens, detector for detecting fluorescence radiation emitted from an end of the fiber responsively to the excitation radiation, and optics frame for mounting all components in fixed relation to the lens for introducing the excitation radiation into the lens within the critical angle.

25 Claims, 5 Drawing Sheets

EVANESCENT WAVE IMMUNOASSAY SYSTEM

BACKGROUND OF THE INVENTION

1. Field of the Invention

This invention relates generally to the field of chemical and immunochemical assay. More specifically, this invention relates to a system for generation of an interrogating beam and its recovery from a test implement utilizing total internal reflection (TIR), and upon a surface of which a reaction has been caused to occur. The portion of the interrogating beam which interacts with reaction products is the evanescent wave. This wave is an electromagnetic component of light which extends less than a wavelength into a surrounding medium. In a system that uses this waveform as a probe, the light is guided by TIR in a rigid rod or bar or fiber of transparent material which is immersed in a fluid medium with a lower index of refraction. The evanescent wave escapes the transparent material and is altered or modified or attenuated by the reaction in the fluid surrounding the transparent member, and then re-enters the member. The degree and mode of modification is a marker of the reaction which is recovered from the transparent member by directing it to a photodetector. The recovered signal is exquisitely sensitive to subtle reactions in the immediate and intimate region of the rigid transparent member surface.

2. Description of the Prior Art

The sensitivity of the evanescent wave has led to a number of prior art attempts to utilize the phenomena in the detecting of subtle but meaningful reactions in immunochemistry. Lackie, in U.S. Pat. No. 5,152,962, builds upon earlier disclosures of Harte, U.S. Pat. No. 4,133,639, and Hirschfeld, U.S. Pat. No. 4,447,546, to teach a rigid transparent rod or fiber into which an interrogating beam is introduced, and reactions near the surface of which are probed by the evanescent wave. The recovery of the evanescent wave is accomplished by so called EPI-optic coaxial arrangements which employ beam splitting elements to separate the recovered signal in another prior art disclosure, Slovacek, U.S. Pat. No. 5,156,976, teaches a conic internal reflection element which is interrogated by an EPI-formoptical train. Much of the prior art is concerned with coupling both interrogating and recovered signal beams to optical forms suitable for immersion in reactive fluid media. An additional prior art item of interest is Shanks et al., U.S. Pat. No. 4,978,503, which discloses a specifically reactive sample collecting and testing device which utilizes a cavity or cavities each having a dimension small enough to enable sample liquid to be drawn into the cavity by capillary action.

These prior art cases and references, however, fail to fully address the controlled introduction of reactant fluid to the transparent surfaces. Further, the cited prior art references employ EPI-illumination techniques which are by nature inefficient, and significantly, do not allow for inclusion of a blank or control optical beam.

It was in light of the state of the technology as just discussed that the present invention was conceived and has now been reduced to practice.

SUMMARY OF THE INVENTION

According to the present invention, apparatus for assaying a fluid sample with radiation capable of exciting fluorescence in fluorescent material comprises a totally internally reflecting, unitary elongated substrate transmissive to both the excitation radiation and to the fluorescence. The fluorescent material includes at least a moiety of an antibody-antigen complex that includes a tag that will provide the fluorescence when excited by an evanescent wave generated by the excitation radiation. The substrate includes an elongated fiber and an integral lens formed to guide the optical radiation into the fiber within the bounds of a critical angle to assure total internal reflectance. A hollow elongated enclosure is disposed concentrically about and spaced from the fiber so as to provide an interspace of capillary dimensions. A test implement supports the elongated substrate, has a reservoir for receiving a fluid sample to be assayed, and is selectively movable to an operative position whereat the fluid sample is caused to flow onto the fiber and, by capillary action, into the interspace between the fiber and the enclosure. The apparatus further includes a source of the excitation radiation, refractive means for focusing the radiation toward the lens, detector means for detecting fluorescence radiation emitted from an end of the fiber responsively to the excitation radiation, and optics frame means for mounting all components in fixed relation to the lens for introducing the excitation radiation into the lens within the critical angle.

A primary object of the present invention is therefore to provide an improved fiber-optic assay system which overcomes a number of the above-noted problems of the prior art.

To this end, it is an object of this invention to provide an efficient optical train which provides a discrete control beam, and a means of optically coupling the optical sources of interrogating, control or blank beams, and recovering the optical signal.

It is a further object of this invention to provide a single-use consumable component comprising the optic forms necessary for efficient optical couplings, and provides for the controlled contact of fluid reactive media to the optical forms necessary for interrogation by the evanescent wave.

It is still a further object of this invention to provide a single use test implement which is an economically efficient article of manufacture.

Another object of the invention is to provide such apparatus as described which is economical to manufacture and to use.

Still another object of the invention is to provide such apparatus which is simple in construction and can be easily used without lengthy explanation.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention and, together with the description, serve to explain the principles of the invention in general terms. Like numbers refer to like parts throughout the disclosure.

DETAILED DESCRIPTION OF THE PREFERRED EMBODIMENTS

Turn now to the drawings and, initially, to FIGS. 1–4 which illustrate most clearly the overall construction of assaying apparatus 20 embodying the present invention. The apparatus 20 serves to assay a fluid sample with excitation radiation from a radiation source in that instance in which the radiation is capable of exciting fluorescence in fluorescent material. The fluorescent material includes at least a moiety of an antibody-antigen complex that includes a tag that will provide the fluorescence when excited by an evanescent wave generated by the excitation radiation.

The apparatus 20 comprises a test implement 22 for supporting an elongated substrate 24. The test implement, preferably fabricated of black polymer resin such as polystyrene or polypropylene filled with carbon black in appropriate proportions, is thus rendered opaque and not reflective. This minimizes unwanted transmission of light energy. Test implement 22 includes a housing having a bottom wall 26 defining a first reservoir 28 for initially containing a fluid sample 29, opposed endwalls 30, 32 upstanding from and integral with the bottom wall and opposed side walls 34, also upstanding from and integral with the bottom wall. The sidewalls 34 and the endwalls 30, 32 are also integral with one another.

Figures 5A, 5B:
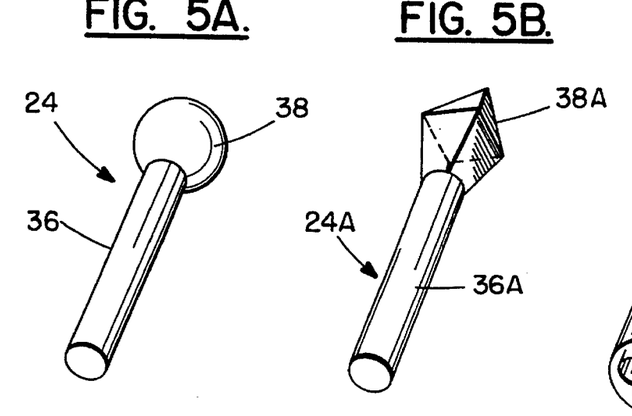
FIG. 5A is a detail perspective view of one embodiment of a component of the test implement illustrated in FIG. 1.
FIG. 5B is a detail perspective view of another embodiment of a component of the test implement illustrated in FIG. 1.

The elongated substrate 24 is of a totally internally reflecting, unitary construction transmissive to both the excitation radiation and to the fluorescence and, as seen particularly well in FIG. 5A, includes an elongated fiber 36 and an integral refraction member 38 in the form of a spherical lens. According to the invention, the radiation is introduced into the lens and at least a portion of the surface of the fiber 36 is adapted to contact the sample. The lens is formed to guide the optical radiation into the fiber 36 within the bounds of a critical angle so as to assure total internal reflectance. In another embodiment, as seen in FIG. 5B, an elongated substrate 24A includes a fiber 36A and an integral refraction member 38A in the form of a prism.

Figure 6:
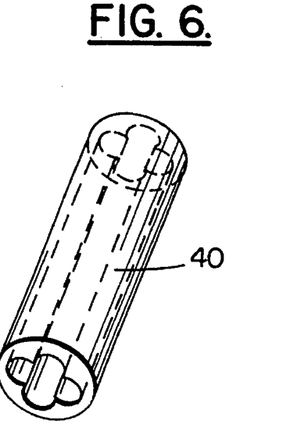
FIG. 6 is a detail perspective view of another component of the test implement illustrated in FIG. 1.
Figure 6A:
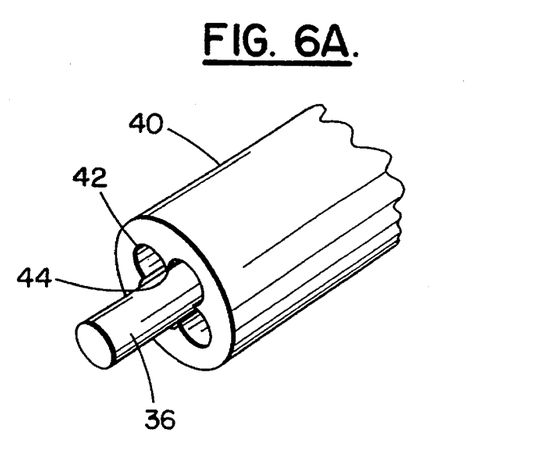
FIG. 6A is a detail perspective view of one embodiment of another component of the test implement illustrated in FIG. 6.
Figure 6B:
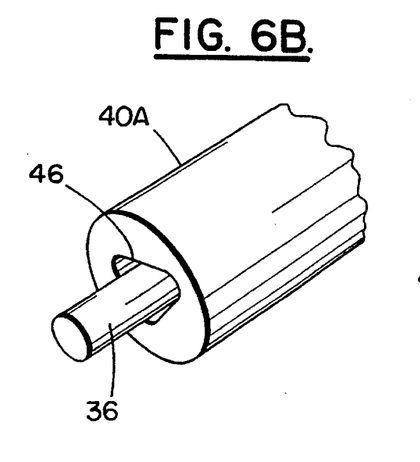
FIG. 6B is a detail perspective view of another embodiment of another component of the test implement illustrated in FIG. 6.

A hollow elongated enclosure 40 (FIG. 6) is disposed about the fiber 36 (FIG. 6A), generally coaxial therewith, and spaced from the fiber so as to provide an interspace 42 of capillary dimension between the fiber and the enclosure. The elongated enclosure extends from a location adjacent the lens or prism to an extreme end distant therefrom. In one embodiment, as seen in FIG. 6A, the elongated enclosure 40 is opaque and includes at least three longitudinally extending ridges 44, equally spaced, circumferentially, for supportive engagement with the fiber. In another embodiment, as seen in FIG. 6B, an elongated enclosure 40A is opaque and includes at least three longitudinally extending similarly dimensioned sidewalls 46 for supportive tangential engagement with the fiber 36.

The endwall 30 has an aperture 48 therethrough and associated conical centering surface 50 for slidably receiving the elongated fiber and for supporting the elongated fiber adjacent the refractive member.

Figure 7:
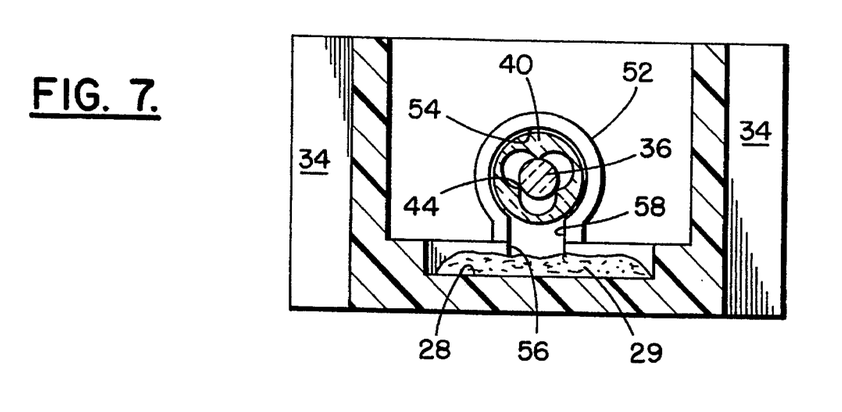
FIG. 7 is a cross section view taken generally along line 7—7 in FIG. 3.

As best seen in FIG. 7, but also seen in FIGS. 1–4, a c-shaped boss member 52 is integral with the endwall 32 and projects toward the endwall 30. The boss member 52 has a cylindrical internal surface 54 for slidable reception of the extremity of the elongated enclosure 40. The cylindrical internal surface 54 defines a second reservoir therein and a channel arrangement interconnecting the first and second reservoirs includes an extension 56 of the first reservoir 28 which is coextensive with a transverse slot 58 in the boss member 52 extending between the first and second reservoirs. This construction assures that the fluid sample will flow freely from the first reservoir to the second reservoir when the test implement is moved from an inoperative position with the bottom wall generally lying in a horizontal plane to an operative position with the endwall 32 generally lying in a horizontal plane.

A bibulous mass member 60, for example, a polymeric open cell foam cylinder, is received in the second reservoir, fittingly engaged with the cylindrical internal surface 54. The elongated enclosure 40 has an annular rim 62 at its extreme end which is in engagement with the bibulous mass member 60. When the test implement is moved from its inoperative position depicted in FIG. 3 to its operative position depicted in FIG. 3A, the fluid sample 29 is caused to flow onto the fiber 36 and, by capillary action, into the interspace 42 between the fiber and the enclosure.

Figure 8:
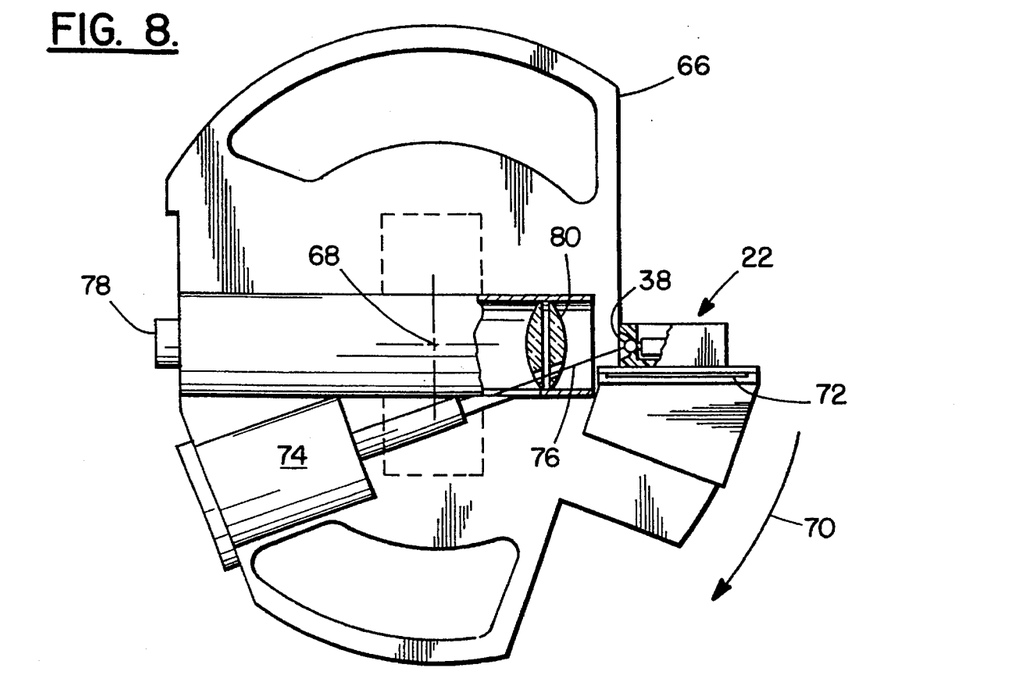
FIG. 8 is a diagrammatic side elevation view of an assaying system embodying the present invention, illustrating one position of the components thereof.
Figure 9:
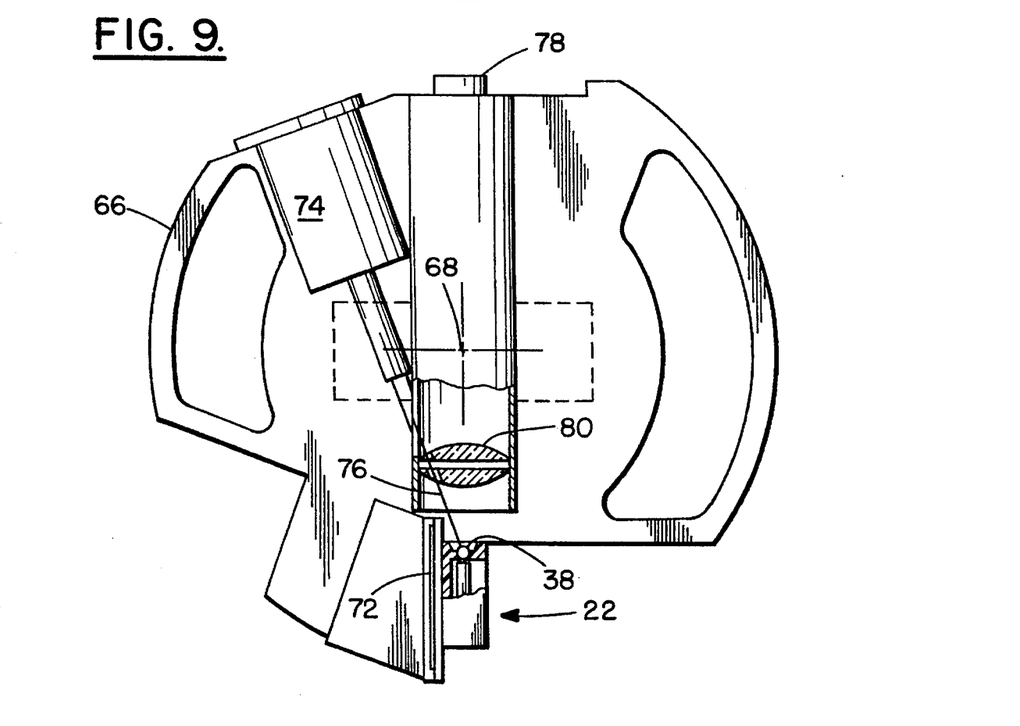
FIG. 9 is a diagrammatic side elevation view of an assaying system embodying the present invention, illustrating another position of the components thereof.

Turn now to FIGS. 8 and 9 which illustrate a complete system 64 for performing an assay of a fluid sample with excitation radiation from a radiation source where the radiation is capable of exciting fluorescence in fluorescent material. An optics frame 66 is suitably mounted for limited rotational movement on a pivot axis 68 in the direction of an arrow 70 between an initial position depicted in FIG. 8 and an assaying position depicted in FIG. 9. The optics frame includes a platform 72 for releasably supporting the test implement 22 and, as just described, is selectively movable to move the test implement between the inoperative position and the operative position. A collimated light source 74, preferably a laser, is suitably mounted on the optics frame for directing an interrogating beam 76 into the refractive member 38. In turn, a suitable detection device 78 such as a photodetector is similarly mounted on the optics frame 66 for receiving reflected light radiation from the elongated substrate 24 through the refractive member 38.

The operation of the assaying system 64 will now be described. The test implement 22 is initially placed on the platform 72 with the fiber 36 in the substantially horizontal position as illustrated in FIG. 8. The fluid sample 29 is placed in the reservoir 28 of the test implement and is not in contact with the surfaces of the fiber 36 or the interior of the enclosure 40, including the longitudinal ridges 44 or the sidewalls 46, depending upon the particular construction of the enclosure. Rotation of the optics frame 66 about the pivot axis 68 through an arc of approximately 90 degrees to the position illustrated in FIG. 9, with the fiber 36 and enclosure 40 in a vertical orientation, causes the fluid sample 29 to flow to contact with and be imbibed by the bibulous mass member 60. The bibulous mass member 60 may contain an appropriate reagent added to the fluid sample. Appropriate reagent refers to a possible inclusion in the foam part of a reactive or trigger chemical. Some reagents are inert until mixed.

Upon filling the available void volume of the bibulous mass member 60, a capillary bridge or closure occurs between the surface of the fiber 36 and the internal surface or surfaces of the enclosure 40. The capillary gradient so established draws the fluid sample 29 from the bibulous mass member 60 and up the interior of the enclosure, that is, the interspace 42, wetting the surface of the fiber and permitting interrogation of the reaction, should any occur, by recovery of the evanescent wave re-entering the fiber after modification by the reaction. Significantly, the capillary forces cannot draw the fluid sample into the capillary bridge unless the bibulous mass member 60 is saturated or oversaturated. If the fluid sample volume exceeds the saturate capacity of the bibulous mass member 60, the enclosure 40 can only fill to its volume, and an equilibrium will occur between the full volume of the interspace 42 and any residue will preferentially remain in the bibulous mass member.

Rotation of the optics frame 66 and all associated components permits optical interrogation to be undisturbed as fluid flow is controlled by gravity, but of course optical rays are not. Mechanical positioning essential to optical consistency is undisturbed. As previously noted, FIG. 8 depicts an initial position of the optics frame 66 and its associated components, with the test implement 22 in the horizontal position, and FIG. 9 depicts a subsequent position of the optics frame and its components rotated to place the test implement in a vertical position for reaction and interrogation.

Figure 10:
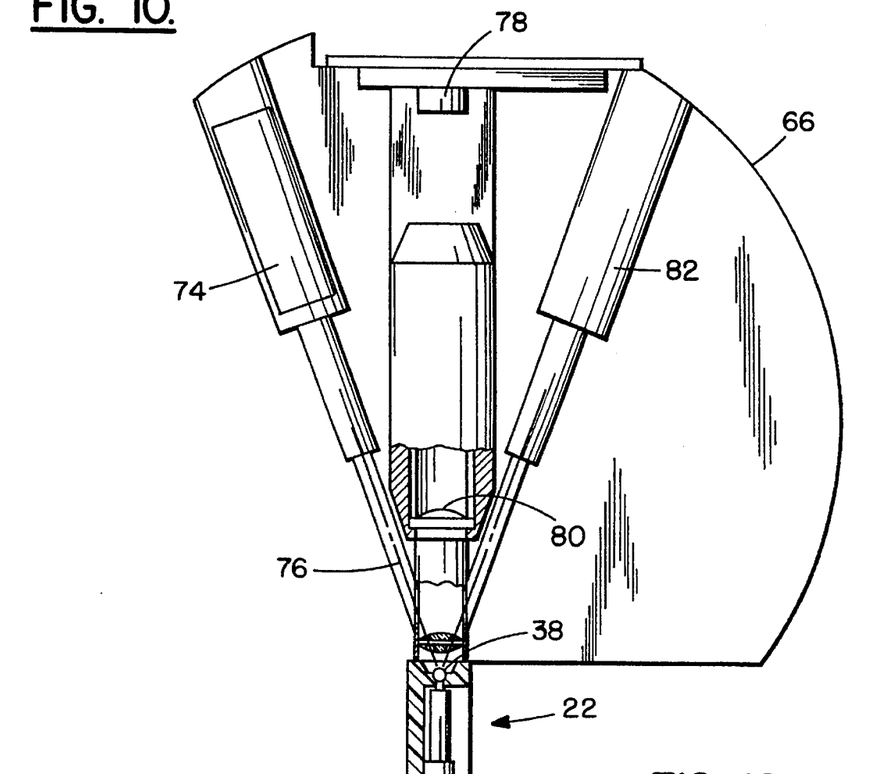
FIG. 10 is a side elevation view, similar to FIG. 9, illustrating another embodiment of the invention.

The refractive member 38 causes the interrogating laser beam 76 to enter the fiber 36 and form evanescent waves on its surface. Modification of those waveforms by chemical activity is detected by the modified optical signal which reenters the fiber and is directed by internal reflectance to emit from the refractive member 38 as a cone of light collected by a detector lens 80 and directed to the photodetector 78. As seen in FIG. 10, a second collimated light source 82, also preferably a laser, and having a different wavelength from that of the interrogating laser beam 76, is mounted on the optics frame 66. The purpose of the second light source of a different wavelength, is to provide a reference beam that is not changed by the rod surface modification derived from the immunochemical reaction. The "non-reactive" beam provides calibration and control of the optical path or "train" in all aspects save for the immunochemical reaction. Note that Lackie teaches a reference beam that compensates for fluctuations in the light source, but the structure of Lackie does not reach or suggest a separate but coincident different wavelength channel or path into the analytic element.

Figure 11:
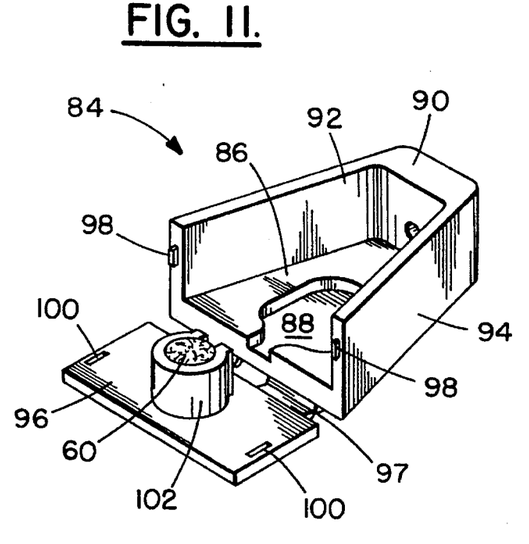
FIG. 11 is a perspective view of a modified test implement also embodying the present invention.
Figure 12:
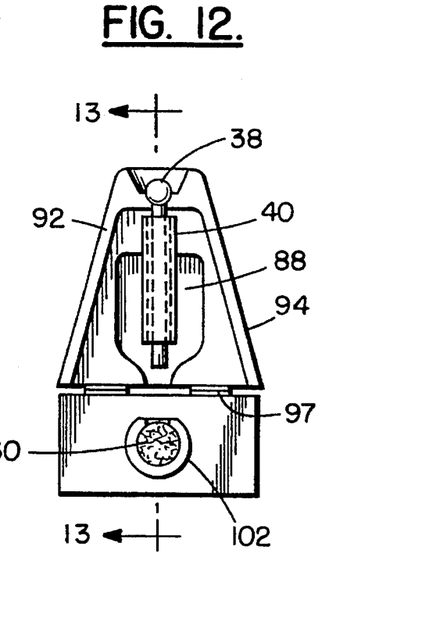
FIG. 12 is a top plan view of the test implement illustrated in FIG. 11.
Figure 13:
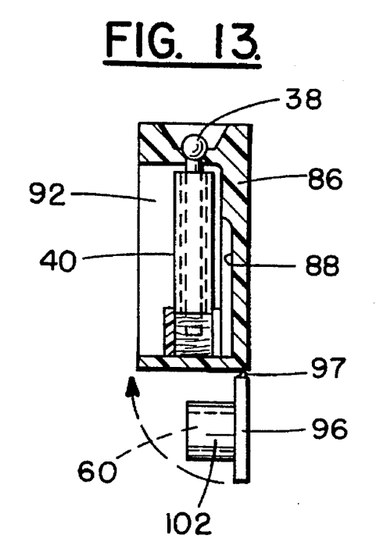
FIG. 13 is a cross section view taken generally along line 13—13 in FIG. 12.

Turn now to FIGS. 11–13 for a description of another embodiment of the test implement 22 of FIGS. 1–4. In this instance, a test implement 84 includes a housing including a bottom wall 86 defining a first reservoir 88 for initially containing the fluid sample. An endwall 90 is upstanding from and integral with the bottom wall and has an aperture therethrough for slidably receiving the elongated fiber 36 and for supporting the elongated fiber adjacent the refractive member 38. Opposed sidewalls 92, 94 are upstanding from and integral with the bottom wall 86. The sidewalls and the endwall 90 are integral. An endwall 96 is pivotally mounted to the bottom wall opposite the endwall 90 for movement between a lowered position generally coplanar with the bottom wall and an upright position upstanding from the bottom wall. Integral, so-called, "living" hinges 97 join the endwall 96 and the bottom wall 86 and provide for such movement.

Mutually engageable locking members 98, 100 on the sidewalls 92, 94 and on the endwall 96, respectively, serve, when engaged, to maintain the endwall 96 in the upright position.

As with the test implement 22, the test implement 84 includes a boss member 102 on the endwall 96 facing the endwall 90 when the endwall 96 is in the upright position and the locking members 98, 100 are engaged. Like the boss member 52, the boss member 102 has a cylindrical internal surface for slidable reception of the extremity of the said elongated enclosure 40 and defining a second reservoir therein for the fitting reception therein of the bibulous mass member 60, previously indicated as preferably being a polymeric open cell foam cylinder. In all other respects, the test implement 84 is similar to the test implement 22.

The construction of the test implement 84 simplifies the insertion of the bibulous mass member 60 into the boss 102 at a time when the endwall 96 is coplanar with the bottom wall 86. Thereafter, the endwall is raised and secured in its upright position. Thereafter, the test implement 84 is mounted on the optics frame 66, the fluid sample 29 is poured into the reservoir, and the optics frame moved from the FIG. 8 position to the FIG. 9 position to enable the assay procedure to proceed.

It was earlier noted that in one embodiment, as seen in FIG. 6A, the elongated enclosure 40 may be opaque and include at least three longitudinally extending ridges 44, equally spaced, circumferentially, for supportive engagement with the fiber. It was also noted that in another embodiment, as seen in FIG. 6B, the elongated enclosure 40A may be opaque and include at least three longitudinally extending similarly dimensioned sidewalls 46 for supportive tangential engagement with the fiber 36. In both instances, by reason of the opaqueness of the enclosure, radiation is prevented from leaking out of the fiber 36 at the point of contact between the fiber and the enclosure with attendant undesirable loss of sensitivity. The distinct advantage of multifoliate, or many leafed, cross sections as illustrated in FIGS. 6A and 6B is as follows: The strength of capillary forces used to fill and hold the fluid under analysis is a function of the cross sectional area and the wetted surface area. Multifoliate cross sections serve to maximize the "fluidic force" and retention force of the capillary space.

Figure 14:
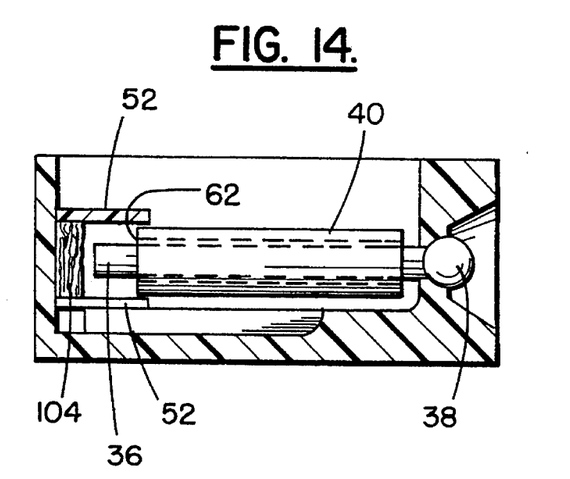
FIG. 14 is a side elevation view, in section, similar to FIG. 3 illustrating another embodiment of the invention utilizing a bibulous mass member in a dried, dense, reduced size condition.
Figure 15:
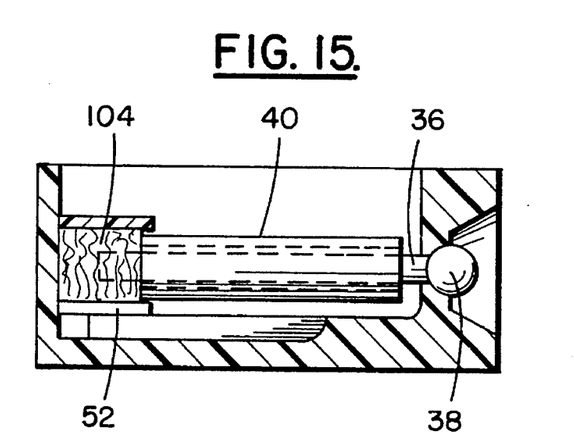
FIG. 15 is a side elevation view, in section, similar to FIG. 14 illustrating the bibulous mass member in a wetted, expanded condition.

Turn now to FIGS. 14 and 15 for a description of another embodiment of the invention. As previously described, the elongated enclosure 40 has an annular rim 62 at its extreme end distant from the refractive member 38 and facing into the interior of the boss member 52. In this instance, a modified bibulous mass member 104 is received in the reservoir defined by the boss member and fittingly engaged with the cylindrical internal surface of the boss member. The bibulous mass member is of a sponge like material which is relatively dense and compact when dry, and therefore, initially distant from the annular rim 62. However, the bibulous mass member is expandable by infusion therein of the fluid sample 29 when the test implement is moved from the inoperative position to the operative position and thereby caused to expand to engage the annular end. When this occurs, the fluid is caused to flow onto the fiber 36 and, by capillary action, into the interspace 42 between the fiber and the enclosure. An example of bibulous material satisfactory for purposes of the invention is that manufactured from polyvinyl alcohol by Kanebo Ltd. of Osaka, Japan and sold under the trademark "BELL ETA".

Figure 1:
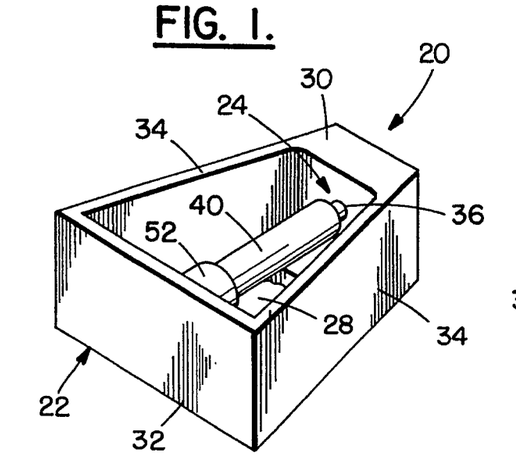
FIG. 1 is a perspective view of a test implement embodying the present invention.
Figure 2:
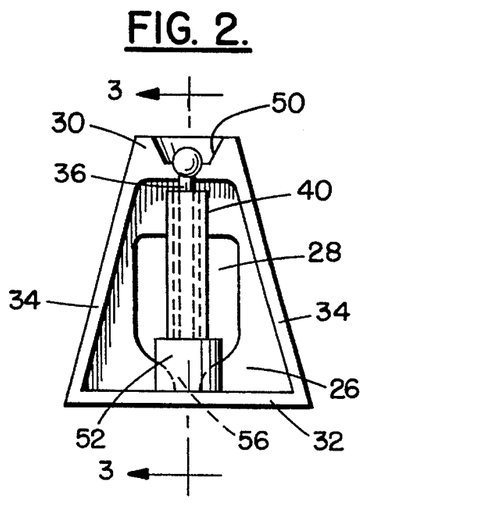
FIG. 2 is a top plan view of the test implement illustrated in FIG. 1.
Figure 3:
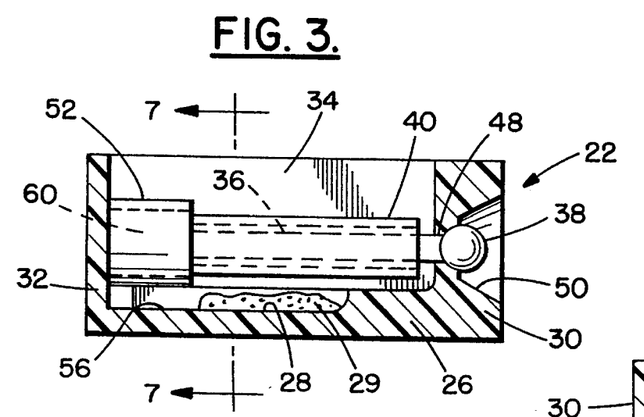
FIGS. 3 and 3A are cross section view taken generally along line 3—3 in FIG. 2.
Figure 3A:
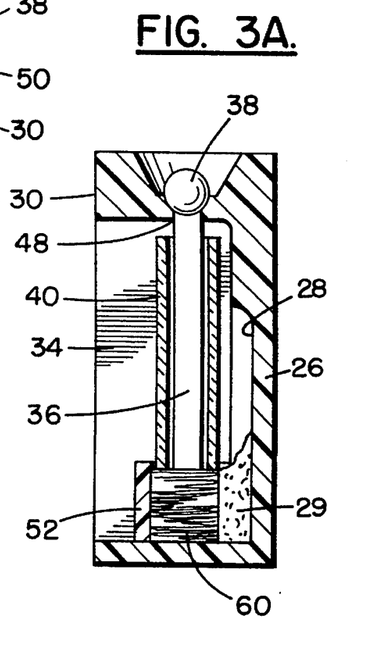
Figure 4:
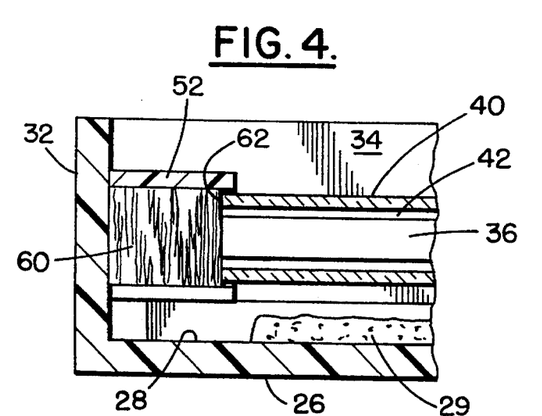
FIG. 4 is an enlarged detail cross section view of a part of FIG. 3.

In FIGS. 3A and 4, the extreme end of the fiber 36 is illustrated as being substantially flush with the annular rim 62 of the enclosure 40. With this construction, the extreme end of the fiber 36 abuts the bibulous mass member 60, but does not penetrate it. This is an acceptable construction. A preferred construction, however, is illustrated in FIGS. 12, 13, 14 and 15 wherein the extreme ends of the fiber 36 protrude beyond the annular rim 62 of the enclosure 40. In this instance, the fiber 36 actually penetrates the bibulous mass member 60 which improves the transfer of the fluid sample from the bibulous mass member onto the fiber.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. Single use disposable apparatus for assaying a fluid sample with excitation radiation from a radiation source, which radiation is capable of exciting fluorescence in fluorescent material, said apparatus comprising:

a totally internally reflecting, unitary elongated substrate transmissive to both the excitation radiation and to the fluorescence, said substrate including an elongated fiber and integral refractive means into which the radiation is to be introduced and at least a portion of the surface of which is adapted to contact the sample, said refractive means being formed to guide the optical radiation into said fiber within the bounds of a critical angle to assure total internal reflectance;

a coating of the fluorescent material on at least a portion of the surface of said fiber;

a hollow elongated enclosure disposed about and spaced from said fiber so as to provide an interspace of capillary dimension between said fiber and said enclosure, said elongated enclosure extending from a location adjacent said lens to an extreme end distant therefrom;

test implement means for supporting said elongated substrate and having reservoir means for receiving a fluid sample to be assayed and being movable between an inoperative position whereat the fluid sample is spaced from the elongated substrate and an operative position whereat the fluid sample is caused to flow onto said fiber and, by capillary action, into the interspace between said fiber and said enclosure.

2. Apparatus as set forth in claim 1 wherein said integral refractive means includes a prism.

3. Apparatus as set forth in claim 1 wherein said integral refractive means is of the same material as said elongated fiber.

4. Apparatus as set forth in claim 1 wherein said test implement means includes:

an internal region defining a first reservoir for initially containing the fluid sample;

support means for supporting said elongated substrate distant from the fluid sample in the first reservoir;

boss means defining a second reservoir for temporarily containing the fluid sample; and channel means extending between the first and second reservoirs for directing flow of the fluid sample from the first reservoir to the second reservoir when said test implement means is moved from the inoperative position to the operative position.

5. Apparatus as set forth in claim 1 wherein the fluorescent material includes at least a moiety of an antibody-antigen complex that includes a tag that will provide the fluorescence when excited by an evanescent wave generated by the excitation radiation.

6. Apparatus as set forth in claim 1 wherein said fiber is disposed coaxially with said enclosure.

7. Apparatus as set forth in claim 1 wherein said elongated enclosure is opaque and includes at least three longitudinally extending ridges equally spaced, circumferentially, for supportive engagement with said fiber.

8. Apparatus as set forth in claim 1 wherein said elongated enclosure is opaque and includes at least three longitudinally extending similarly dimensioned sidewalls for supportive tangential engagement with said fiber.

9. Apparatus as set forth in claim 1 wherein said integral refractive means includes a lens.

10. Apparatus as set forth in claim 9 wherein said lens includes a spherical lens having an index of refraction matched to that of said fiber.

11. Apparatus as set forth in claim 1 including:

a source of the excitation radiation;

said refractive means being operable for focusing said radiation toward said lens;

detector means for detecting fluorescence radiation emitted from an end of said fiber responsively to the excitation radiation; and optics frame means for mounting said source, said refractive means, and said detector means in fixed relation to said lens for introducing the excitation radiation into said lens within the critical angle.

12. Apparatus as set forth in claim 11 including:

test implement means for operatively supporting said substrate on said optics frame means.

13. Apparatus as set forth in claim 1 wherein said test implement means includes:

a housing having opposed first and second endwalls, said first endwall having an aperture therethrough for slidably receiving said elongated fiber and for supporting said elongated fiber adjacent said refractive means;

an internal region intermediate said first and second endwalls defining a first reservoir for initially containing the fluid sample;

boss means on said second endwall facing said first endwall having a cylindrical internal surface for slidable reception of said extremity of said elongated enclosure, said cylindrical internal surface defining a second reservoir therein for temporarily containing the liquid sample; and channel means extending between the first and second reservoirs for directing flow of the fluid sample from the first reservoir to the second reservoir when said test implement means moves from the inoperative position to the operative position.

14. Apparatus as set forth in claim 13 wherein said elongated enclosure has an annular rim at said extreme end; and including:

bibulous mass means received in the second reservoir and fittingly engaged with said cylindrical internal surface of said boss means, said bibulous mass means being initially distant from said annular rim, said bibulous mass means being expandable by infusion therein of the fluid sample when said test implement is moved from the inoperative position to the operative position and thereby caused to expand to engage said annular end, such that the fluid is caused to flow onto said fiber and, by capillary action, into the interspace between said fiber and said enclosure.

15. Apparatus as set forth in claim 13 including:

bibulous mass means received in the second reservoir and fittingly engaged with said cylindrical internal surface of said boss means, said elongated enclosure having an annular rim at said extreme end in engagement with said bibulous mass means.

16. Apparatus as set forth in claim 15 wherein said bibulous mass means includes a polymeric open cell foam cylinder.

17. Apparatus as set forth in claim 1 wherein said test implement means includes:

a housing having a bottom wall defining a first reservoir for initially containing the fluid sample, opposed first and second endwalls upstanding from and integral with said bottom wall, said first endwall having an aperture therethrough for slidably receiving said elongated fiber and for supporting said elongated fiber adjacent said refractive means, and opposed first and second side walls upstanding from and integral with said bottom wall, said sidewalls and said endwalls being integral with one another;

c-shaped boss means on said second endwall projecting toward said first endwall having a cylindrical internal surface for slidable reception of said extremity of said elongated enclosure, said cylindrical internal surface defining a second reservoir therein; and channel means including a transverse slot in said boss means extending between the first and second reservoirs for directing flow of the fluid sample from the first reservoir to the second reservoir when said test implement means moves from the inoperative position to the operative position.

18. Apparatus as set forth in claim 17 including:

bibulous mass means received in the second reservoir and fittingly engaged with said cylindrical internal surface of said boss means, said elongated enclosure having an annular rim at said extreme end in engagement with said bibulous mass means.

19. Apparatus as set forth in claim 18 wherein said bibulous mass means includes a polymeric open cell foam cylinder.

20. Apparatus as set forth in claim 1 wherein said test implement means includes:

a housing including:

a bottom wall defining a first reservoir for initially containing the fluid sample;

a first endwall upstanding from and integral with said bottom wall, said first endwall having an aperture therethrough for slidably receiving said elongated fiber and for supporting said elongated fiber adjacent said refractive means;

opposed first and second side walls upstanding from and integral with said bottom wall, said sidewalls and said first endwall being integral with one another;

a second endwall;

hinge means pivotally mounting said second endwall to said bottom wall for movement between a lowered position generally coplanar with said bottom wall and an upright position upstanding from said bottom wall;

mutually engageable locking means on said sidewalls and on said second endwall for maintaining said second endwall in the upright position;

boss means on said second endwall facing said first endwall having a cylindrical internal surface for slidable reception of said extremity of said elongated enclosure, said cylindrical internal surface defining a second reservoir therein; and channel means extending between the first and second reservoirs for directing flow of the fluid sample from the first reservoir to the second reservoir when said second endwall moves from the lowered position to the upright position.

21. Apparatus as set forth in claim 20 including:

bibulous mass means received in the second reservoir and fittingly engaged with said cylindrical internal surface of said boss means.

22. Apparatus as set forth in claim 21 wherein said bibulous mass means includes a polymeric open cell foam cylinder.

23. A single use disposable system for assaying a fluid sample with excitation radiation from a radiation source, which radiation is capable of exciting fluorescence in fluorescent material and recovering a coupled evanescent wave, said apparatus comprising:

a totally internally reflecting, unitary elongated substrate transmissive to both the excitation radiation and to the fluorescence, said substrate including an elongated fiber and integral refractive means into which the radiation is to be introduced and at least a portion of the surface of which is adapted to contact the sample, said refractive means being formed to guide the optical radiation into said fiber within the bounds of a critical angle to assure total internal reflectance;

a coating of the fluorescent material on at least a portion of the surface of said fiber;

a hollow elongated enclosure disposed about and spaced from said fiber so as to provide an interspace of capillary dimension between said fiber and said enclosure, said elongated enclosure extending from a location adjacent said lens to an extreme end distant therefrom;

test implement means for supporting said elongated substrate and having reservoir means for receiving a fluid sample to be assayed and being movable between an inoperative position whereat the fluid sample is spaced from the elongated substrate and an operative position whereat the fluid sample is caused to flow onto said fiber and, by capillary action, into the interspace between said fiber and said enclosure;

optics frame means including a platform for supporting said test implement means and being selectively movable to move said test implement means between the inoperative position and the operative position;

collimated light source means for directing an interrogating beam into said refractive means when said test implement means is in the operative position; and detector means for receiving reflected light radiation from said substrate through said refractive means coupled to an evanescent wave.

24. A system as set forth in claim 23 wherein said collimated light source means includes a laser.

25. A system as set forth in claim 23 wherein said detector means includes a photodetector.

* * * * *